Figure 1:
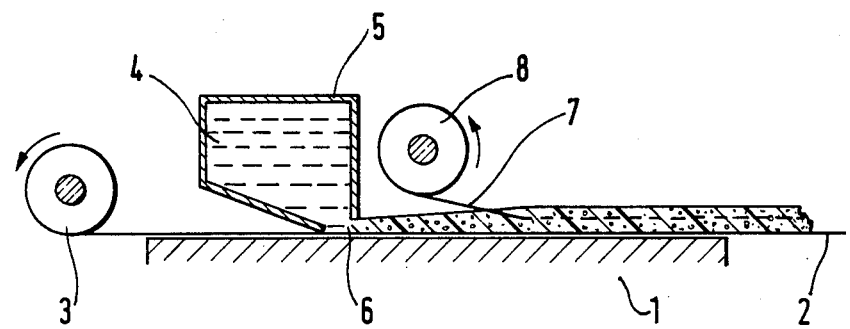

United States Patent [19]

Naylor et al.

[11] Patent Number: 4,572,814
[45] Date of Patent: Feb. 25, 1986

[54] MEDICAL-SURGICAL DRESSING AND A PROCESS FOR THE PRODUCTION THEREOF

[75] Inventors: Clifford Naylor, Dinas Powis; David Pocknell, Rhoose, both of Wales

[73] Assignee: Dow Corning, Ltd., Barry Wales, Wales

[21] Appl. No.: 509,496

[22] Filed: Jun. 30, 1983

[30] Foreign Application Priority Data

Jul. 6, 1982 [GB] United Kingdom ............... 8219448

[51] Int. Cl.⁴ .................... B29C 67/22; A61F 13/00
[52] U.S. Cl. .................... 264/46.4; 128/155; 264/45.8; 264/46.7; 264/54; 264/DIG. 5
[58] Field of Search ............. 264/45.3, 46.2, 46.4, 264/46.7, 45.8, 54, DIG. 5; 128/155

[56] References Cited

U.S. PATENT DOCUMENTS

| | | | |
|---|---|---|---|
| 2,540,906 | 2/1951 | Overton et al. | 264/45.3 X |
| 3,007,205 | 11/1961 | House | 264/257 X |
| 3,298,884 | 1/1967 | Willy | 264/46.2 X |
| 3,439,676 | 4/1969 | Burda | 128/268 |
| 3,648,692 | 3/1972 | Wheeler | 128/156 |
| 3,763,858 | 10/1973 | Buese | 128/155 X |
| 4,349,020 | 9/1982 | Kirkorian | 128/155 |

FOREIGN PATENT DOCUMENTS

| | | |
|---|---|---|
| 798667 | 7/1958 | United Kingdom . |
| 867619 | 5/1961 | United Kingdom . |
| 1064462 | 4/1967 | United Kingdom . |
| 1522637 | 8/1978 | United Kingdom . |
| 1542657 | 3/1979 | United Kingdom . |
| 1543215 | 3/1979 | United Kingdom . |

Primary Examiner—Philip Anderson
Attorney, Agent, or Firm—Howard W. Hermann

[57] ABSTRACT

A medical-surgical dressing comprising a reinforced sheet of silicone elastomer foam having a thickness not exceeding 10 millimeters, one of the surfaces of the sheet having a surface layer of open cell foam and the other surface having a substantially non-cellular surface skin. The dressing may be manufactured by a process comprising depositing a liquid foamable silicone composition on an absorbent surface, allowing the composition to foam and set to an elastomer and thereafter separating the foam sheet from the substrate.

The dressings are useful e.g. for the treatment of wounds, burns and as liners for plaster casts.

4 Claims, 2 Drawing Figures

U.S. Patent  Feb. 25, 1986  4,572,814

MEDICAL-SURGICAL DRESSING AND A PROCESS FOR THE PRODUCTION THEREOF

This invention relates to a surgical or medical dressing suitable for use in the treatment of burns and other injury, and also relates to a process for the production of such a dressing.

The treatment of burns and wounds has historically involved the application of sterile fibrous dressings such as gauze and lint, with or without the conjoint use of antiseptic or curative substances. Such materials tend to stick to the surface being treated or leave fibres in the wound. More recent developments have involved the application of synthetic films and sponges to the injury. For example U.S. Pat. No. 3,439,676 describes a wound dressing which is a band of self-adhering silicone elastomer impregnated with a medicament. However, such a dressing is non-absorbent with regard to the exudations normally present.

U.S. Pat. No. 3,648,692 describes a surgical dressing comprising a facing layer of neutral thrombogenic reticulated open cell foam material and a mutually secured co-extensive, gas permeable, microporous backing. The preferred foam material is stated therein to be polyurethane foam and the backing may be of, for example polypropylene, teflon or silicone rubber. However, the manufacture of such a dressing requires that the backing and foam layers be preformed and then subsequently brought together with an adhesive in a laminating operation.

According to the present invention there is provided a medical-surgical dressing comprising a reinforced sheet of silicone elastomeric foam having a thickness of not greater than 10 millimetres, one surface of the said sheet having a surface layer of open cell foam and the other surface having a substantially noncellular surface skin.

The dressings of this invention comprise sheets of silicone elastomeric foam wherein the broad surface intended for contact with the body has an open cell foam structure and the outer surface comprises a substantially non-cellular skin. In order to improve its resistance to tearing or other damage during use the foam dressing is reinforced with a suitable fibrous or weblike material, for example nylon or polyester net. The dressings have a thickness not greater than 10 mm and preferably have a thickness of from about 3 to about 6 mm.

One method of producing dressings according to this invention involves depositing a foamable silicone elastomer composition on a substrate and allowing it to foam whereby a substantially non-cellular, continuous skin forms at the exposed surface. During foaming a reinforcing web may be embedded in the foam. When cured the upper portion of the foam block may be cut away to provide a sheet having the desired reinforcement and surface characteristics. Such a method, however, poses several problems. For example, it is difficult to cut accurately thin sections of an elastomeric foam. The method is also wasteful since only the upper portion of the foam can be used to provide a sheet with the desired surfaces.

We have discovered that it is possible to obtain the foam dressings of this invention by a novel method which avoids the disadvantages associated with the above described procedure. Accordingly this invention also includes a process for the manufacture of a medical-surgical dressing which comprises applying a layer of a liquid foamable or foaming silicone elastomer composition to a substrate having a surface which is an absorbent for the liquid composition, adding a reinforcing material to the foamable or foaming composition such that it becomes embedded therein, allowing the mixture to foam or continue foaming and to set to an at least partially cured silicone elastomer foam and thereafter separating the foam layer from the substrate.

In the performance of the process of this invention any liquid foam-forming silicone elastomer composition may be employed. The preferred compositions for use according to this invention are those which comprise a polydiorganosiloxane having hydroxyl groups, a siloxane having silicon-bonded hydrogen atoms, a curing catalyst and a hydroxylated compound. They are normally made available as a two package product. When the contents of the packages are mixed in the appropriate proportions the mixture foams and subsequently sets to an elastomeric sponge. Compositions of this type are described in, for example U.K. Patent Nos. 798 667, 867 619, 1 064 462 and 1 543 215. Foam-forming compositions comprising organopolysiloxanes having silicon-bonded unsaturated groups, organosilicon compounds having silicon-bonded hydrogen atoms and an addition catalyst e.g. chloroplatinic acid may also be employed. Such compositions are described in, for example, U.K. Patent Nos. 1 522 637 and 1 542 657. Desirably the composition will be free of additives which may impart irritant or toxic properties to the dressing, especially when the dressing is to be employed in direct contact with the body for the treatment of open wounds or burns. The substrate receiving the liquid foam composition should be sufficiently porous to be absorbent with regard to the composition. A preferred substrate material is a non-glazed paper which permits slight penetration of the liquid foam composition into its porous surface.

Fabrication of the dressing according to the novel process of this invention is conveniently carried out by preparing the liquid foamable composition and applying it while still in the flowable state to the substrate. Depending on the rate of the chemical reaction involved the composition may at this stage be a liquid or may have already commenced expansion into a foam. Application of the composition may be carried out employing any suitable means, for example from a hopper having a lower transverse aperture or by way of a traversing dispensing nozzle which may be associated with a mixing head. The depth of the resulting foam appropriate to the desired thickness of the dressing can be controlled by the amount of foamable liquid employed and/or by the use of a scraper blade or an equivalent depth controlling device. A preferred method of depth/thickness control in the process of this invention comprises passing the substrate carrying the foamable or foaming composition beneath a slowly rotating roller positioned horizontally and transversely with respect to the direction of motion of the substrate. Any build up of cured or partially cured foam composition on the roller surface which may occur during operation may be readily removed therefrom by means of a scraper blade or similar device.

The process may be carried out batchwise or, more preferably, can also be performed as a continuous or semi-continuous operation. Thus for example the foamable or foaming composition may be poured into a stationary receptacle or on to the moving substrate which is supplied from a roll or other source and thus itself forms, or is supported by, a conveyor belt.

Prior to the curing of the foam into a solid elastomer it is necessary to embed therein a suitable reinforcing material. This can be conveniently accomplished by placing a sheet of reinforcing material on the surface of the still liquid foamable or foaming composition after pouring and allowing or causing it to penetrate the composition to the desired depth. The actual depth of penetration of the reinforcing material is not critical provided that the material does not prevent the attainment of the desired skin-like or porous configurations of the respective surfaces of the dressing. In order to permit the ready penetration of the reinforcing material according to this technique the material should be sufficiently perforate or porous to permit flow-through of the foamable or foaming composition. A preferred reinforcing material is a textile net fabric, particularly of synthetic fibre, for example nylon, polyester, polypropylene or acrylic fibre.

Depending on the type of foam forming composition employed the foam sheet may be allowed to cure to an elastomeric solid at normal ambient temperatures or it may be desirable or necessary to hasten the cure by the application of heat.

When the composition has cured to an elastomeric solid it is removed from the substrate. In some cases it may be possible to separate the foam and substrate by carefully pulling them apart. However, in order to avoid the possibility of tearing the sheet it is preferred that separation be facilitated by the use of a parting knife or similar cutting edge placed against the substrate. Any cutting edge or blade will suffice provided it is sufficiently sharp to cut the foam away from the substrate.

Figure 2:
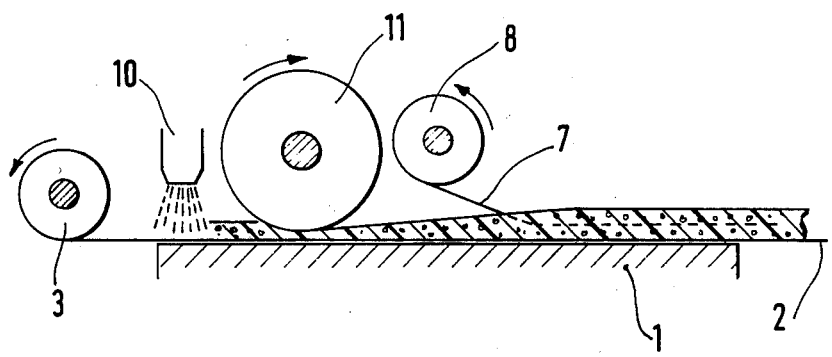

Exemplary means for carrying out the process of this invention are shown in FIGS. 1 and 2 of the drawings hereof which are sectional views in side elevation. In FIG. 1, a table or other rigid surface 1 supports a flexible absorbent substrate 2 which is drawn from a roll or other source 3. The foamable silicone elastomer composition 4 is applied to the surface of the substrate 2 from a hopper 5 having a transverse slot 6. A reinforcing material 7 is drawn from a roll 8 and embedded in the liquid foamable composition.

FIG. 2 illustrates a modification of the means shown in FIG. 1 wherein the hopper 5 is replaced by a dispensing head 10 which may be adapted to traverse the support transversely with respect to its direction of motion. A rotatable roller 11 is positioned above the substrate receiving the foamable composition and transversely with respect to the direction of motion thereof. If desired the roller may be provided with a scraper blade (not shown) which functions to remove from the roller any accretion of cured or partially cured elastomeric foam.

The foam sheet may be produced in the final desired configuration, for example in the form of a narrow bandage or broad sheet, or it may be cut to the desired size and shape after curing. If desired the dressing may be subjected to elevated temperatures to increase the degree of cure, remove volatile substances or to effect sterilisation. Sterilisation may also be achieved by chemical means, such as by exposure to ethylene oxide. The dressing may also be washed in water if necessary to remove unwanted residues. If desired the dressing may be coated or impregnated with a medicament, for example an antiseptic, antibiotic or other substance for the control of infection.

Possible applications for the dressings of this invention include their use as wound and burn dressings, as swabs and as liners for location between plaster casts and the body.

The following example illustrates the invention. A composition containing a silanol end-stopped polydimethylsiloxane, having a viscosity of approximately 2000 cP at 25° C., a trimethylsilyl end-stopped methylhydrogen polysiloxane, a low molecular weight hydroxylated methyl siloxane, a diatomaceous earth and stannous octoate as catalyst was prepared by thoroughly mixing the components.

The liquid mixture was then pumped into a box resting in contact with a porous paper substrate having a width of about 25 cm and supported on a rigid horizontal surface. The forward wall of the box was cut so that a gap of approximately 2 mm existed between the lower edge of the wall and the substrate. The floor of the box adjacent to this edge was also cut away thus permitting the liquid foam composition to be drawn forward with the paper.

Foaming of the composition occurred shortly after deposition on the paper. At the commencement of foaming the paper was drawn forward. Simultaneously a nylon net fabric having a mesh size of approximately 2 mm was drawn from a roll situated above the foam and allowed to sink into the foam under a slight downward tension. The process was terminated after several metres of the paper substrate had been drawn off and the foam-coated substrate allowed to stand for 30 minutes to ensure that cure had proceeded to a sufficient degree to produce an elastomeric solid. A large blade palette knife was then inserted at the interface between the substrate and the foam and employed to cut the foam from the paper.

The product was a flexible, reinforced elastomeric foam sheet having a thickness of about 5 mm. The upper surface of the sheet had a substantially continuous skin whilst the lower surface had a cellular structure. After washing to remove unreacted materials, and sterilisation the sheet was suitable for use as a medical-surgical dressing.

That which is claimed is:

1. A process for the manufacture of a medical-surgical dressing having one open cellular surface and a substantially non cellular surface skin as its opposite surface, said process comprising applying a layer of a liquid foamable or foaming silicon elastomer composition to a substrate having a surface which is an absorbent for the liquid composition, embedding a sheet of reinforcing material in the layer of foamable or foaming composition, allowing the mixture to foam or continue foaming and to set to an at least partially cured silicon elastomer foam and thereafter separating the foam layer from the substrate to thereby form the open cellular surface at the surface formed by separation from the substrate.

2. A process as claimed in claim 1 wherein the absorbent substrate is a non-glazed paper.

3. A process as claimed in claim 1 wherein separation is effected by means of a cutting edge.

4. A process as claimed in any one of claims 1 to 3 wherein the separated foam sheet is subjected to a sterilisation treatment.

* * * * *